(12) United States Patent
Li et al.

(10) Patent No.: US 11,494,908 B2
(45) Date of Patent: Nov. 8, 2022

(54) MEDICAL IMAGE ANALYSIS USING NAVIGATION PROCESSING

(71) Applicant: SHENZHEN KEYA MEDICAL TECHNOLOGY CORPORATION, Shenzhen (CN)

(72) Inventors: Ruoping Li, Shenzhen (CN); Pengfei Zhao, Shenzhen (CN); Junhuan Li, Shenzhen (CN); Bin Ouyang, Shenzhen (CN); Yuwei Li, Bellevue, WA (US); Kunlin Cao, Kenmore, WA (US); Qi Song, Seattle, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 0 days.

(21) Appl. No.: 17/408,321

(22) Filed: Aug. 20, 2021

(65) Prior Publication Data
US 2022/0301154 A1 Sep. 22, 2022

(51) Int. Cl.
*G06K 9/00* (2022.01)
*G06T 7/00* (2017.01)
(Continued)

(52) U.S. Cl.
CPC ............ *G06T 7/0012* (2013.01); *G06F 40/20* (2020.01); *G06K 9/629* (2013.01); *G06K 9/6217* (2013.01);
(Continued)

(58) Field of Classification Search
CPC ...................................................... G06K 9/62
See application file for complete search history.

(56) References Cited

U.S. PATENT DOCUMENTS 7,058,210 B2    6/2006  Mundy et al.
9,316,713 B2 *  4/2016  Iwadate ............... G01R 33/543
(Continued)

FOREIGN PATENT DOCUMENTS

CN    106780475 A    5/2017
CN    106934799 A    7/2017
(Continued)

OTHER PUBLICATIONS

Decision to Grant in corresponding Chinese Application No. 202110299397.9 dated May 28, 2021 (4 pages).
(Continued)

*Primary Examiner* — Hadi Akhavannik
(74) *Attorney, Agent, or Firm* — Bayes PLLC (57) ABSTRACT

The present disclosure relates to a medical image analysis method, a medical image analysis device, and a computer-readable storage medium. The medical image analysis method includes receiving a medical image acquired by a medical imaging device; determining a navigation trajectory by performing navigation processing on the medical image based on an analysis requirement, the analysis requirement indicating a disease to be analyzed; extracting an image block set along the navigation trajectory; extracting image features using a first learning network based on the image block set; and determining an analysis result using a second learning network based on the image features and the navigation trajectory.

18 Claims, 7 Drawing Sheets

(51) Int. Cl.
  *G06K 9/62* (2022.01)
  *G06F 40/20* (2020.01)
  *G16H 30/20* (2018.01)
  *G16H 10/60* (2018.01)
  *G06N 3/08* (2006.01)
  *G06V 10/50* (2022.01)

(52) U.S. Cl.
  CPC ........... *G06K 9/6267* (2013.01); *G06N 3/084* (2013.01); *G06V 10/50* (2022.01); *G16H 10/60* (2018.01); *G16H 30/20* (2018.01); *G06T 2207/20021* (2013.01); *G06T 2207/20081* (2013.01); *G06T 2207/20084* (2013.01); *G06T 2207/30016* (2013.01); *G06T 2207/30056* (2013.01); *G06T 2207/30096* (2013.01); *G06T 2207/30101* (2013.01); *G06T 2207/30172* (2013.01); *G06T 2207/30241* (2013.01); *G06V 2201/031* (2022.01)

(56) References Cited

U.S. PATENT DOCUMENTS

| | | | | |
|---|---|---|---|---|
| 2004/0267153 | A1* | 12/2004 | Bergethon | A61B 5/4076 600/554 |
| 2009/0270720 | A1* | 10/2009 | Iwadate | G01R 33/546 600/413 |
| 2010/0074493 | A1* | 3/2010 | Wiemker | A61B 6/12 382/130 |
| 2017/0116497 | A1* | 4/2017 | Georgescu | G16H 50/70 |
| 2019/0021677 | A1* | 1/2019 | Grbic | A61B 5/7292 |

FOREIGN PATENT DOCUMENTS

| | | |
|---|---|---|
| CN | 110866184 A | 3/2020 |
| CN | 111209916 A | 5/2020 |
| CN | 111275706 A | 6/2020 |
| CN | 111968044 A | 11/2020 |
| CN | 112508918 A | 3/2021 |

OTHER PUBLICATIONS

First Office Action in corresponding Chinese Application No. 202110299397.9, dated May 6, 2021 (10 pages).

\* cited by examiner

MEDICAL IMAGE ANALYSIS USING NAVIGATION PROCESSING

CROSS REFERENCE TO RELATED APPLICATIONS

The application is based upon and claims the benefit of priority to Chinese Patent Application No. 202110299397.9, filed Mar. 22, 2021, the entire content of which is incorporated herein by reference in its entirety.

TECHNICAL FIELD

The present disclosure relates to the technical field of medical image processing, and more specifically, to a medical image analysis method and device, a computer apparatus, and a computer-readable storage medium.

BACKGROUND

Medical imaging can quickly, non-invasively or minimally invasively capture structural and functional images of human internal tissues, thus facilitating clear understanding of the physical structure and metabolic state of human organs. Medical image analysis therefore has become an indispensable auxiliary tool for clinical diagnosis. Through image processing technology and computer vision technology, images can be effectively processed for computer-aided diagnosis and surgical planning, etc., which enjoys broad applications and provides great social benefits.

In recent years, Deep Learning (DL), especially Deep Convolutional Neural Network (CNN), has rapidly developed into a research hotspot of medical image analysis. DL can automatically extract hidden disease diagnosis features from medical image data, so it has gradually become an important technology in image screening and classification.

However, conventionally, when detecting and analyzing medical images, only a single disease can be detected and analyzed using a single model. For example, a breast cancer classification model is used to detect and analyze breast cancer, a nuclear cataract classification model is used to detect and analyze nuclear cataract, or an Alzheimer Disease (AD) and Mild Cognitive Impairment (MCI) classification model is used to detect and analyze Alzheimer Disease and Mild Cognitive Impairment. In clinical applications, it is often beneficial to analyze a plurality of different types of diseases based on the same image. However, the existing technologies would require multiple models to analyze different types of diseases. Therefore, when analyzing medical images, one has to manually adjust the setting requirements of models for different diseases, resulting in low efficiency and high labor cost for medical image analysis. In addition, the existing technology can only analyze the whole medical image, but cannot perform the analysis for disease areas of concern, which leads to high computational cost, low efficiency and low accuracy in the medical image analysis. The existing technologies therefore cannot meet the requirements of accurate analysis and diagnosis of diseases in clinical applications.

The present disclosure provides improved medical image analysis methods and systems in light of the above-mentioned problems.

SUMMARY

The present disclosure provides a medical image analysis method, a medical image analysis device, and a computer-readable storage medium. According to the exemplary medical image analysis method, a navigation trajectory is determined by performing a navigation processing on a received medical image based on an analysis requirement, and an analysis result is determined based on an image block set extracted along the navigation trajectory by using a first learning network and a second learning network. Using the disclosed image analysis method, the medical image can be analyzed more accurately and pertinently, thus reducing the computational complexity of medical image processing, improving the efficiency and accuracy of medical image analysis and reducing the labor cost.

According to a first aspect of the present disclosure, a medical image analysis method is provided. The medical image analysis method includes: receiving a medical image acquired by a medical imaging device; determining a navigation trajectory by performing a navigation processing on the medical image based on an analysis requirement, where the analysis requirement indicates a disease to be analyzed; extracting an image block set along the navigation trajectory; extracting image features based on the image block set using a first learning network; and determining an analysis result using a second learning network based on the extracted image features and the navigation trajectory.

According to a second aspect of the present disclosure, a medical image analysis device is provided. The medical image analysis device includes: a communication interface configured to receive a medical image acquired by a medical imaging device; and a processor configured to determine a navigation trajectory by performing navigation processing on the medical image based on an analysis requirement, where the analysis requirement indicates a disease to be analyzed; extract an image block set along the navigation trajectory; extract image features using a first learning network based on the image block set; and determine an analysis result using a second learning network based on the extracted image features and the navigation trajectory.

According to a third aspect of the present disclosure, a non-transitory computer-readable storage medium is provided with computer program instructions stored thereon, where a medical image analysis method is performed when the computer program instructions are executed by a processor.

With the disclosed medical image analysis method and device, and the computer-readable storage medium according to embodiments of the present disclosure, the model framework can be uniformly applied to address different analysis requirement through the use of a navigation trajectory. For example, the model framework can analyze different diseases according to different requirements. The user can obtain respective navigation trajectories by inputting different analysis requirements (e.g., the types of disease), thus avoiding the complicated operation of changing different model settings according to the different requirements, and reducing the labor cost. Furthermore, by using the navigation trajectory, the disclosed analysis method can produce more useful information given a relatively small amount of input information. In other words, under the uniform framework, targeted and more representative information can be extracted from image blocks according to different analysis requirements. In addition, the method further determines the analysis result based on the image block set extracted along the navigation trajectory by using deep learning networks (e.g., the first learning network and the second learning network). As a result, medical images can be more accurately and efficiently analyzed according to the analysis requirements to provide more accurate and targeted diagnosis. Therefore, the complexity of medical image processing is reduced, and the efficiency and accuracy of medical image analysis are improved.

BRIEF DESCRIPTION OF THE DRAWINGS

In the drawings, which are not necessarily drawn to scale, like reference numerals may describe similar components in different views. Like reference numerals having letter suffixes or different letter suffixes may represent different instances of similar components. The drawings illustrate generally, by way of example, but not by way of limitation, various embodiments, and together with the description and claims, serve to explain the disclosed embodiments. Where appropriate, the same reference numerals are used in all drawings to refer to the same or similar parts. Such embodiments are demonstrative and not intended to be exhaustive or exclusive embodiments of the present device or method.

DETAILED DESCRIPTION

In order to make those skilled in the art to better understand technical solutions of the present disclosure, the present disclosure will be described in detail with reference to the accompanying drawings and specific embodiments. The embodiments of the present disclosure will be further described in detail with reference to the drawings and specific embodiments, but not as a limitation of the present disclosure. The order of steps in which they are described as an example herein should not be regarded as a limitation, and those skilled in the art should know that the order can be altered as appropriate.

In addition, it should be understood by those of ordinary skill in the art that the drawings provided herein are for the purpose of illustration, and the drawings are not necessarily drawn to scale.

In the description of the present disclosure, it is to be understood that terms "first", "second" and the like are merely used for the purpose of description and cannot be understood to indicate or imply relative importance or the relative order they have to occur.

Hereinafter, a medical image analysis method and device according to embodiments of the present disclosure will be described in detail with reference to the accompanying drawings.

Figure 1:
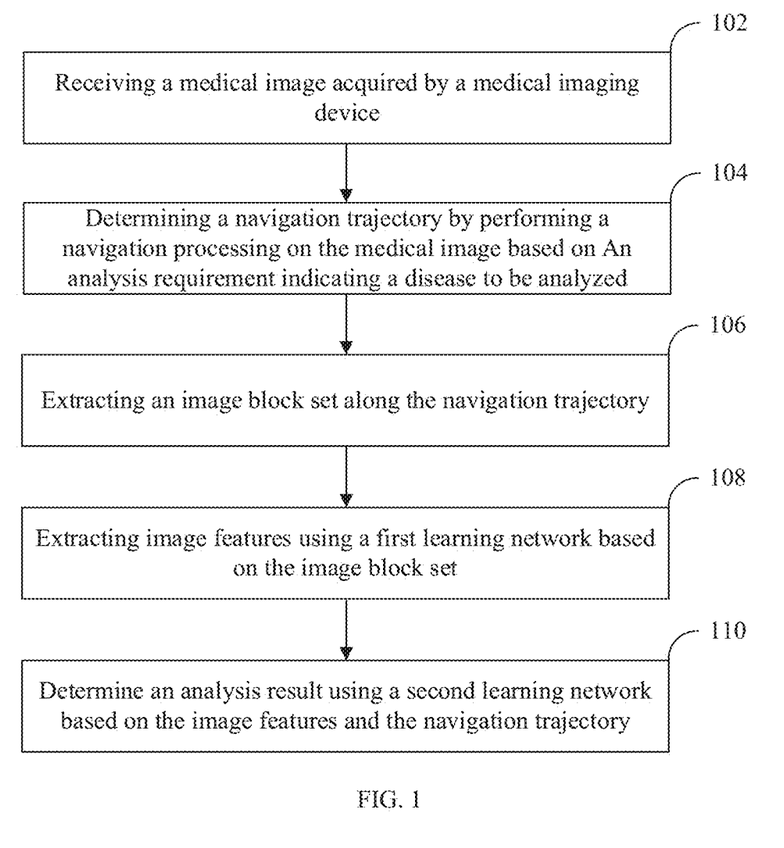
FIG. 1 shows a flowchart of a medical image analysis method according to an embodiment of the present disclosure.

FIG. 1 shows a flowchart of a medical image analysis method according to an embodiment of the present disclosure. As shown in FIG. 1, the medical image analysis method may include a step of receiving a medical image acquired by a medical imaging device (step 102).

In some embodiments, a computer apparatus (e.g., a medical image analysis device) receives the medical image acquired by the medical imaging device. Here, the computer apparatus may be a smart phone, a tablet computer, a notebook computer, a desktop computer, a smart speaker, a smart watch, etc., which is not limited by the embodiments of the present disclosure. Furthermore, the computer apparatus may obtain the medical image from the medical imaging device in real time, or from a server that stores the previously acquired medical images. Here, the server may be an independent physical server, such as Picture Archiving and Communication Systems (PACS), a server cluster or distributed system composed of a plurality of physical servers, or a cloud server that provides cloud computing services such as cloud services, cloud databases, cloud computing, cloud functions, cloud storage, network services, cloud communication, middleware services, domain name services, security services, CDN, and big data and artificial intelligence platforms, etc. The computer apparatus and the server may be directly or indirectly connected through wired or wireless communication, which is not limited by the embodiments of the present disclosure.

The medical imaging device may include X-ray, but not limited to, imaging equipment, Magnetic Resonance Imaging (MM) imaging equipment, ultrasound imaging equipment, nuclear medicine imaging device, thermal imaging equipment, medical optical imaging equipment, etc. The medical image is an image acquired by a medical imaging equipment. The medical image may include X-ray image (for example, Computed Tomography (CT) image), MM image, ultrasound image, radionuclide image, etc., which is not limited by the embodiments of the present disclosure. The medical image may be a two-dimensional (2D) or three-dimensional (3D) image, and the 3D image may include a plurality of 2D image slices. Furthermore, the medical image may be a liver and kidney image, a chest image, or an image of other parts, which is not limited by the embodiments of the present disclosure.

In some embodiments, the medical image analysis method may further include a step of determining a navigation trajectory by performing a navigation processing on the medical image based on an analysis requirement (step 104), wherein the analysis requirement indicates a disease to be analyzed.

In some embodiments, after receiving the medical image, the computer apparatus performs the navigation processing on the received medical image based on the analysis requirement and obtains a corresponding navigation trajectory. Here, the analysis requirement may indicate the disease to be analyzed, such as a brain tumor, a breast cancer, etc. In some embodiments, it may also indicate a target region to be analyzed, such as a coronary artery, a head and neck artery, etc. In some additional embodiments, it may also include a manual/automatic setting for navigation, such as more than one key points on the boundary of a liver and a kidney that are manually labelled/automatically detected. In some embodiments, the analysis requirement may further include requirements customized by the user (e.g., physician) according to different application scenarios or requirements, which are not limited by the embodiments of the present disclosure.

The navigation processing may apply a classification learning network established based on a deep learning training process. The navigation trajectory may be in different forms for different analysis requirements (e.g., different disease types). For example, the navigation trajectory may be directional, and may include a path or pattern of key points. As another example, the navigation trajectory may be a corresponding template of structural or functional regions that are associated with each other. As a further example, the navigation trajectory may be a regional path, a one-way path, a complete path, a closed-loop path, a tree-like structure, a graphical structure, etc., which are not limited by the embodiments of the present disclosure.

Figure 2A:
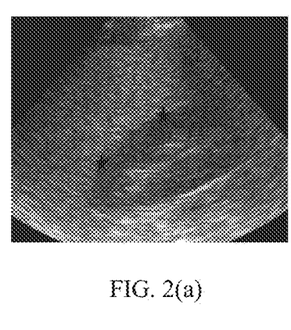
FIGS. 2(a)-2(f) show schematic diagrams of navigation trajectories according to embodiments of the present disclosure.
Figure 2B:
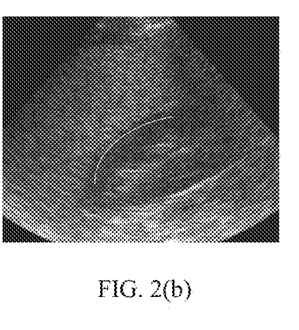
Figure 2C:
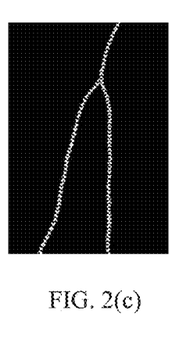
Figure 2D:
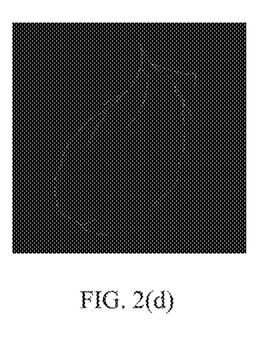
Figure 2E:
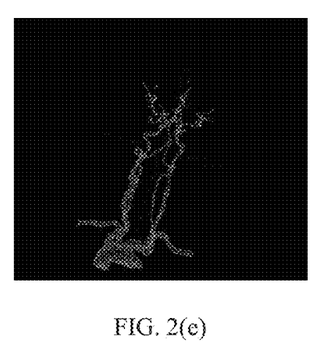

Exemplarily, for the classification of a fatty liver, the navigation trajectory may be formed by more than one key points on the boundary of a liver and a kidney that are manually labelled or automatically detected, as shown in FIG. 2(a). It may also be a boundary line of the liver and the kidney that is manually labelled, as shown in FIG. 2(b). For vascular lesions detection, the navigation trajectory may be along the direction of blood vessel segments formed by key points that are manually labelled/automatically detected, as shown in FIG. 2(c). It may also be a complete or partial blood vessel centerline that is automatically computed, as shown in FIG. 2(d). For head and neck detection, the navigation trajectory may be a point cloud of a head or neck artery that is manually sketched/automatically detected, as shown in FIG. 2(e).

Figure 2F:
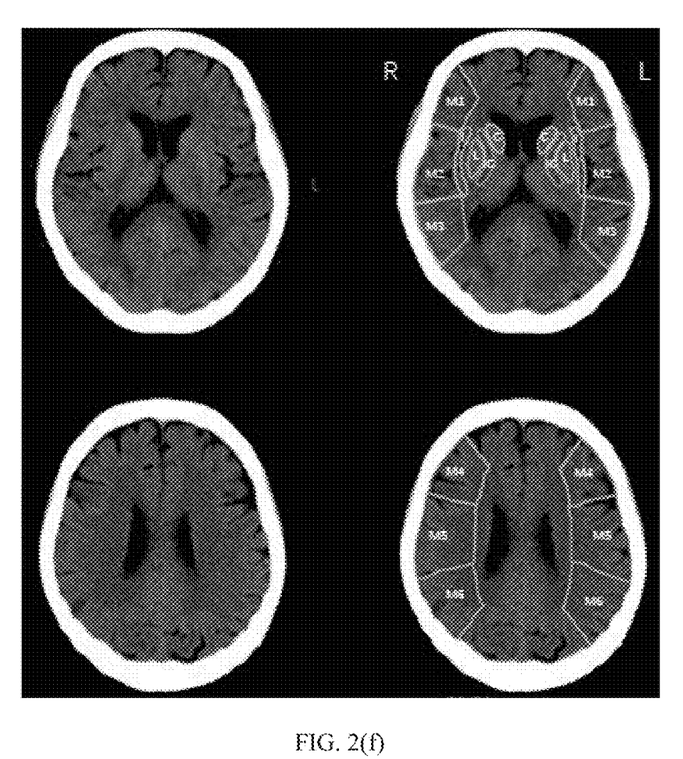

Exemplarily, for cerebral ischemia detection, the navigation trajectory may be a corresponding template of structure or functional regions corresponding to left and right brains that is manually sketched or automatically detected/registered. As shown in FIG. 2(f), images in the upper left and upper right corners are an original brain image of a sagittal section view of a three-dimensional brain map and an image after structural partitioning, respectively; and images in the lower left and lower right corners are an original brain image of another sagittal section view of the three-dimensional brain map and an image after structural partitioning, respectively.

For example, as shown in the image located in the upper right corner of FIG. 2(f), the side close to "L" is the left brain, and the side close to "R" is the right brain. Left and right brain regions marked with the same name are corresponding structural regions. It can be seen from the image that the left and right brains each include M1, M2, M3, C, L, I and IC regions. That is, the M1 region in the left brain corresponds to the M1 region in the right brain, the M2 region in the left brain corresponds to the M2 region in the right brain, the M3 region in the left brain corresponds to the M3 region in the right brain, the C region in the left brain corresponds to the C region in the right brain, and so on. For another example, as shown in the image located in the lower right corner of FIG. 2 (f), the left and right brains respectively include M4, M5 and M6 regions, that is, the M4 region in the left brain corresponds to the M4 region in the right brain, the M5 region in the left brain corresponds to the M5 region in the right brain, and the M6 region in the left brain corresponds to the M6 region in the right brain. When training the network, each pair of associated structural regions may be input together for classification training and prediction of ischemia or not. It should be noted that data for training the network is properly paired according to the association, that is, the M1 region in the left brain will not be associated with the M2 region in the left brain, and the M1 region in the left brain will not be associated with the M2 region in the right brain, either.

By inputting a pair of the structurally/functionally associated regions as a set, the model merely needs to analyze the associated regions, which improves the analysis efficiency while obtaining more accurate analysis results.

In some embodiments, the medical image analysis method may further include a step of extracting an image block set along the navigation trajectory (step 106).

In some embodiments, the computer apparatus may input the medical image into a preset segmentation network, and perform image segmentation on the medical image along the navigation trajectory to obtain the image block set. In some embodiments, the segmentation network for segmenting the medical image may be a machine learning network such as a multi-level learning network, and may be trained using supervised learning. The architecture of the segmentation network may include a stack of different blocks and layers, each of which converts more than one input into more than one output. Examples of different layers may include more than one convolution layers or full convolution layers, non-linear operator layers, pooling layers or sub-sampling layers, full connection layers and/or final loss layers, and each layer may be connected to an upstream layer and a downstream layer. Furthermore, the segmentation network may be a traditional network such as V-Net and U-Net, or a Pyramid Scene Parsing Network (PSPNet), or a DeepLabV3 network, which is not limited by the embodiments of the present disclosure.

Image segmentation refers to dividing the image into several regions according to features such as gray scale, color, spatial texture, geometric shape, etc., so that these features show consistency or similarity in the same region, but show noticeable differences among different regions. Image segmentation methods based on deep learning may include, but are not limited to, image segmentation methods based on feature coding, image segmentation methods based on region selection, image segmentation methods based on a recurrent neural network, image segmentation methods based on upsampling/deconvolution, image segmentation methods based on improved feature resolution, image segmentation methods based on feature enhancement, image segmentation methods using Conditional Random Field (CRF)/Markov Random Field (MRF), etc.

The navigation trajectory may include the path or pattern of the key points or the corresponding template of structural or functional regions that are associated with each other according to the analysis requirements. Therefore, each image block in the image block to be extracted may be functionally or spatially associated. Therefore, by extracting the image block set along the navigation trajectory, the amount of information of image blocks to be analyzed can be reduced. That is, using the navigation trajectory helps collect more useful information at the cost of a relatively small amount of information.

Figure 3:
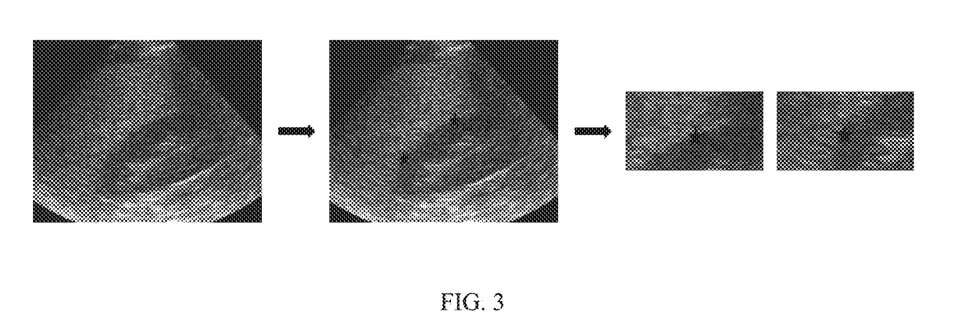
FIG. 3 shows a schematic diagram of extracting image block sets according to an embodiment of the present disclosure.

As an example, the input medical image is a 2D liver and kidney ultrasound image. As shown in FIG. 3, after receiving the 2D liver and kidney ultrasound image acquired by the ultrasound imaging device, the computer apparatus performs a navigation processing on the 2D liver and kidney ultrasound image to determine the navigation trajectory (e.g., two key points "★" shown in FIG. 2(a)). Then, the computer apparatus intercepts the 2D liver and kidney ultrasound image with the two key points "★" as the center respectively to obtain two 2D image blocks, and the collective of the two 2D image blocks is the image block set. When determining whether there is fatty liver and its severity, the brightness ratio of liver and kidney is an important index. Therefore, the key points or paths for the boundary between the two organs are used as the navigation trajectory, and the image blocks to be analyzed are intercepted along the navigation trajectory. The image blocks can contain both the brightness information of liver and kidney at the same time, making the analysis results more reasonable and accurate.

In some embodiments, the medical image analysis method may further include a step of extracting image features using a first learning network based on the image block set (step 108).

In some embodiments, the first learning network may include a CNN. CNN is a type of Feedforward Neural Network (FNN) which contains convolution calculation and has a deep structure. A convolutional neural network has the ability of representing learning, and may invariantly classify input information according to its hierarchical structure. The extracted image features may include color features, texture features, shape features and spatial relationship features. Further, the image features may be a sequence of image block features in the image block set.

Feature extraction is a concept in computer vision and image processing, which refers to extracting image information by using computer to determine whether each image point has an image feature. The result of feature extraction is to divide points on the image into different subsets each forming isolated points, continuous curves or continuous regions. Methods of feature extraction may include, but not limited to, Scale-Invariant Feature Transform (SIFT), Histogram of Oriented Gradient (HOG), Speeded Up Robust Feature (SURF), Difference of Gaussian (DOG), etc.

In some embodiments, the medical image analysis method may further include a step of feeding the extracted image features to a second learning network (step 110), where the second learning network is configured to determine an analysis result based on the image features and the navigation trajectory.

In some embodiments, the computer apparatus feeds the extracted image features to the second learning network, so that the second learning network may analyze the medical image based on the image features and the navigation trajectory to obtain the analysis result. Here, the second learning network may include one or a combination of a recurrent neural network and a recursive neural network. The recurrent neural network is a type of recursive neural network, which takes sequence data as input and recurses in the evolution direction of the sequence. In a recurrent neural network, all nodes (recurrent units) are connected in chain. Recursive neural network is an Artificial Neural Network (ANN) which has a tree-like hierarchical structure and includes network nodes that recur input information according to their connection order. The recurrent neural network is one of the deep learning algorithms. In some embodiments, the information flows between the nodes of the second learning network may follow the physical (including but not limited to space, physiological function, etc.) constraint relationship between the points on the corresponding navigation trajectory, thus obtaining more accurate analysis results.

Exemplarily, for the detection of brain tumors, prediction and analysis may be made based on the navigation trajectory as a template for the brain structural or functional regions and by using a 3D CNN. For the detection of vascular diseases, 2D/3D CNNs may be used, and the prediction and analysis may be made based on the key points of a certain segment of a blood vessel as the navigation trajectory, combined with the recurrent neural network or recursive neural network.

With the medical image analysis method according to the embodiments of the present disclosure, the model framework can be uniformly applied to address different analysis requirement through the use of the navigation trajectory. The model framework can perform image analysis according to different requirements for different diseases. For example, the user can obtain the respective navigation trajectories by inputting the different analysis requirements (e.g., types of diseases), thus avoiding the complicated operation of changing a plurality of model settings according to the different requirements, and reducing the labor cost. Furthermore, by using the navigation trajectory, the disclosed analysis method can produce more useful information given a relatively small amount of input information. In other words, under the uniform framework, targeted and more representative information can be extracted from image blocks according to different analysis requirements. In addition, the method further determines the analysis result based on the image block set extracted along the navigation trajectory by using deep learning networks (e.g., the first learning network and the second learning network). As a result, medical images can be more accurately and efficiently analyzed according to the analysis requirements to provide more accurate and targeted diagnosis. Therefore, the complexity of medical image processing is reduced, and the efficiency and accuracy of medical image analysis are improved.

In some embodiments, the image features are a sequence of image block features in the image block set. The second learning network is configured to learn a spatial/functional relationship based on the image block features extracted by the first learning network and the navigation trajectory, and determine the analysis result based on the learned spatial/functional relationship between the image block features.

The spatial relationship refers to the relative spatial position or directional relationship between a plurality of objects segmented in the image, which may include a connection/adjacency relationship, an overlapping/overlaying relationship and an inclusion/containment relationship. In some embodiments, two methods may be used to extract spatial relationship features of the image: one is to automatically divide the image into objects or color regions, then extract image features according to these regions and establish indices; and the other is to evenly divide the image into several regular sub-blocks, and then extract features of each image sub-block and establish the indices. In some embodiments, the functional relationship is, for example, a functional association between left and right brain regions, etc.

In some embodiments, the medical image analysis method further includes: receiving a medical record of a subject of the medical image; screening out relevant texts of the analysis requirements from the medical record; extracting text features based on the relevant texts; fusing the text features and the image features to obtain fused features; and feeding the fused features to the second learning network to determine the analysis result.

In some embodiments, the computer apparatus screens out texts relevant to the analysis requirements from the received medical record of the subject of the medical images, and extracts the text features based on the relevant texts. Furthermore, the computer apparatus performs a feature fusion on the text features and the image features to obtain the fused features, and feeds the fused features to the second learning network, so that the second learning network may determine the analysis result based on the fused features.

In some embodiments, the medical record may be a written record made by a medical staff during the illness and treatment of patients, which is the basis for doctors to diagnose and treat diseases and valuable for medical scientific research. The medical records may include basic information (e.g., name, gender, age, marriage, etc.), main complaint, present medical history (e.g., onset time, priority, location, characteristics and changes of accompanying symptoms, etc.), past medical history (e.g., past health conditions, presence or absence of infectious diseases, presence or absence of a history of surgery, presence or absence of a history of food or drug allergy, etc.), personal history (e.g., whether life is regular, presence or absence of any bad habits, presence or absence of a history of major mental trauma, etc.), family history (e.g., presence or absence of a family genetic disease, presence or absence of a family cluster disease, presence or absence of similar diseases among family members, etc.). The criteria of screening cases may include, but are not limited to, criteria of case inclusion and exclusion, classification criteria, etiological grouping criteria, age grouping criteria, and prognosis grouping criteria. The cases may be screened manually or automatically, which is not limited by the embodiments of the present disclosure.

Text feature extraction may extract features that can effectively represent the overall information of the text from the text. Text feature extraction can achieve effective dimension reduction of text vector space from a high-dimensional map to a low-dimensional map, and can screen out categorization features. The methods of text feature extraction may include, but are not limited to, transforming original features into fewer new features by mapping or transformation, selecting some of the most representative features from the original features, selecting the most influential features according to the knowledge of experts, and selecting, with mathematical methods, features with the most valuable information for classification.

In an embodiment of the present disclosure, the text features may be extracted based on relevant texts and using a Natural Language Processing (NLP) model. Here, natural language processing is a subject that takes language as the object and uses computer technology to analyze, understand and process natural language. That is, natural language processing takes computer as a powerful tool for language research, carries out quantitative research on language information with the support of computer, and provides language description that can be jointly used by human and computer. Natural language processing includes Natural Language Understanding (NLU) and Natural Language Generation (NLG). The natural language processing model may be a language model, or an N-gram model, or a Neural Network Language Model (NNLM), which is not limited by the embodiments of the present disclosure.

Feature fusion may integrate features from different sources and removes redundancy, so as to obtain the fused features which are more conducive to the prediction and analysis of medical images. Feature fusion algorithms may include, but are not limited to, feature fusion algorithms based on Bayesian theory (for example, multiplication rules and addition rules of classifiers, feature fusion algorithms based on linear feature dependency model, etc.), feature fusion algorithms based on the sparse representation theory, feature fusion algorithms based on the deep learning theory, etc. The feature fusion algorithms based on the sparse representation theory can extract multiple features from the sample and then establish a feature joint sparse matrix which is the result of the multi-feature fusion. The feature fusion algorithms based on the deep learning theory can fuse the features obtained from a plurality of neural networks to acquire fused features.

In some embodiments, fusing the text features and the image features to obtain fused features further includes: merging the text features and the image features, feeding the merged features into a multilayer perceptron, and optimizing the merged features through back propagation to obtain the fused features.

In some embodiments, the computer apparatus performs feature merging on the text features and the image features, and inputs the merged features into the multi-layer perceptron. Furthermore, the computer apparatus optimizes the merged features by using the back propagation algorithm to obtain the fused features.

Feature merging may superimpose features from different sources to obtain the merged features which are more conducive to the prediction and analysis of medical images. Methods of feature merging may include the ADD method and the CONCAT method. For network structures such as ResNet/FPN, feature merging involves superimposing values element by element while the number of channels stays the same, and thus the ADD method can be used. For network structures such as DenseNet, feature merging involves merging the channels, and thus the CONCAT method can be used. That is, the CONCAT method is to merge features, fuse features extracted by a plurality of convolution feature extraction frameworks, or fuse information of an output layer; and the ADD method is to superpose information. Further, the ADD method increases the amount of information describing features of an image in each dimension without changing the dimensions, which is beneficial to the final image classification. The CONCAT method merges the number of the channels, that is, the dimensions of describing features of an image are increased, while the amount of information of the features in each dimension is unchanged.

The Multilayer Perceptron (MLP) is a feedforward artificial neural network model, which maps a plurality of input data sets to a single output data set. Furthermore, the multilayer perceptron is a neural network architecture with multiple hidden layers in addition to the input layer and output layer.

Back propagation (BP) algorithm is a learning algorithm suitable for multilayer neural networks, and it is based on gradient descent method. The main idea of the BP algorithm is to input training set data into the input layer of the artificial neural network, pass through the hidden layer, and finally reach the output layer and output the result, which is the forward propagation process of the artificial neural network. The error between the estimated value and the actual value is calculated, and the error is back propagated from the output layer to the hidden layer until it is propagated to the input layer. In the process of back propagation, the values of various parameters are adjusted according to the error, and the above process is iterated continuously until convergence.

Figure 4:
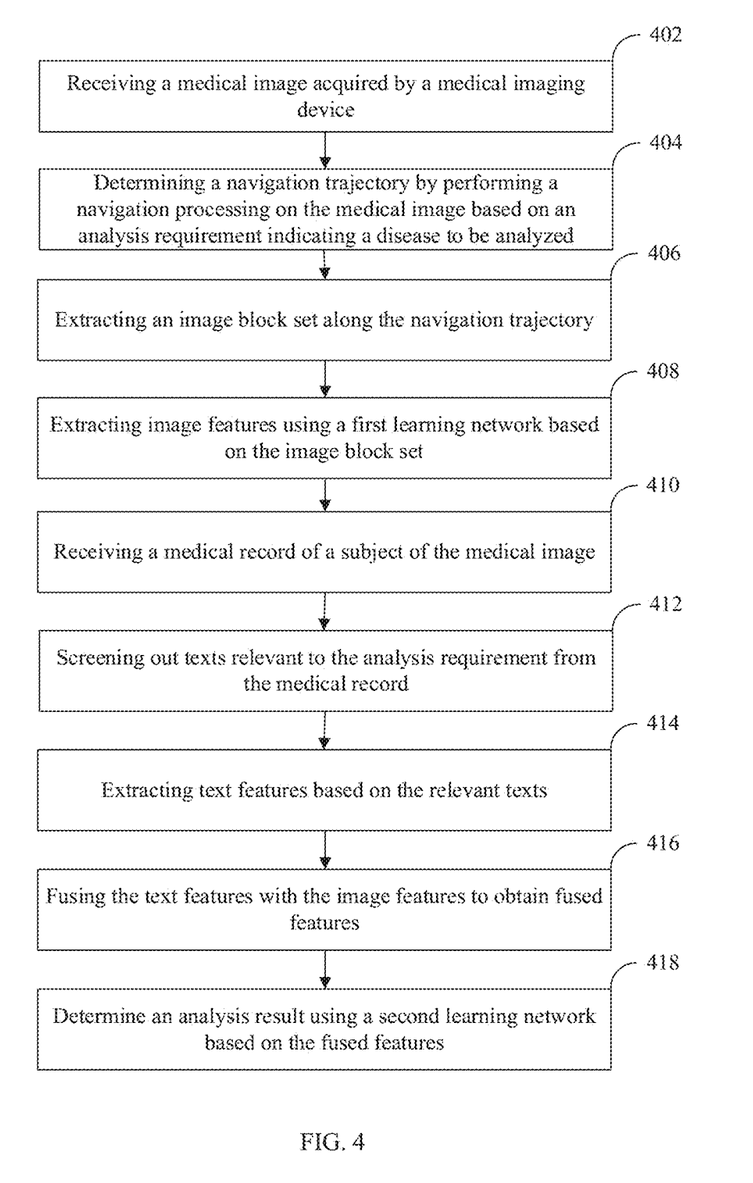
FIG. 4 shows a flowchart of a medical image analysis method according to an embodiment of the present disclosure.

FIG. 4 shows a flowchart of a medical image analysis method according to an embodiment of the present disclosure. As shown in FIG. 4, the medical image analysis method includes the following steps. The method starts with receiving a medical image acquired by a medical imaging device (step 402). The method may further include a step of performing a navigation processing on the medical image based on an analysis requirement to obtain a navigation trajectory (step 404), and the analysis requirement indicates a disease to be analyzed. The method may further include a step of extracting an image block set along the navigation trajectory (step 406). The method may further include a step of extracting image features using a first learning network based on the image block set (step 408). The method may further include a step of receiving a medical record of a subject of the medical image (step 410). The method may further include a step of screening out texts relevant to the analysis requirement from the medical record (step 412). The method may further include a step of extracting text features based on the relevant texts (step 414). The method may further include a step of fusing the text features and the image features to obtain fused features (step 416). The method may further include a step of feeding the fused features to a second learning network (step 418), to determine an analysis result based on the fused features.

In the medical image analysis method according to the embodiment of the present disclosure, the navigation trajectory is obtained by performing the navigation processing on the received medical image based on the analysis requirement, and the image features are extracted based on the image block set extracted along the navigation trajectory by using the first learning network. The text features extracted from the relevant texts screened out from the medical record are fused with the extracted image features to obtain the fused features, and the analysis result is determined based on the fused features by using the second learning network. Applying the second learning network to the fused features can reduce the interference of redundant information, so that medical images related to the analysis requirement can be analyzed more accurately and pertinently. Therefore, the disclosed method utilizes information more effectively, reduces complexity of the medical image processing, improves the efficiency and accuracy of the medical image analysis, and reduces the labor cost.

Figure 5:
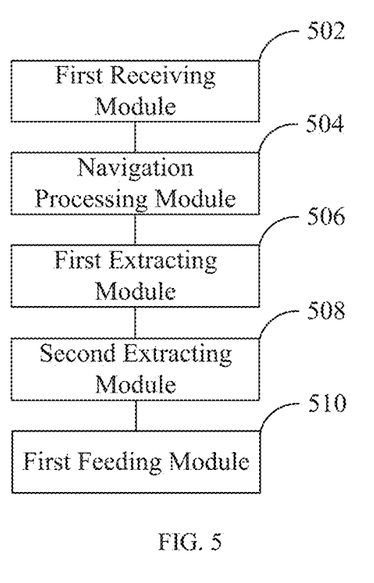
FIG. 5 shows a block diagram of an exemplary medical image analysis device according to an embodiment of the present disclosure.
Figure 6:
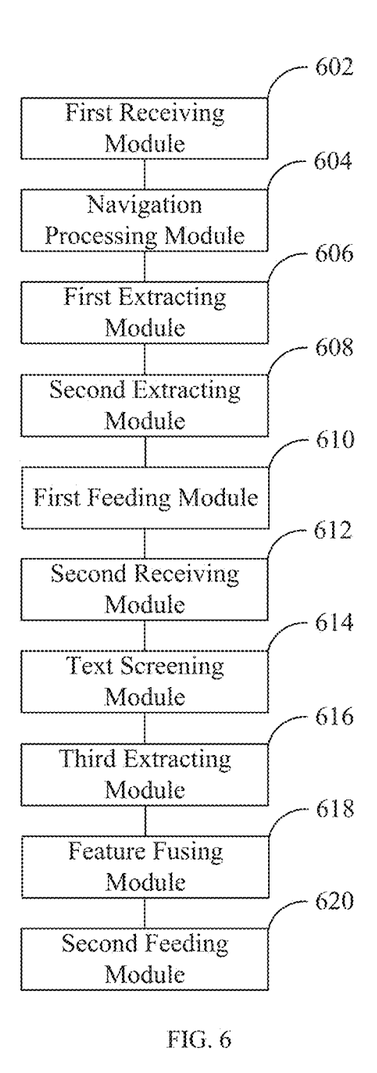
FIG. 6 shows a block diagram of another exemplary medical image analysis device according to an embodiment of the present disclosure.

FIGS. 5 and 6 show device embodiments of the present disclosure, which can be used to implement the method embodiments of the present disclosure. For details that are already disclosed in connection with the method embodiments, they will not be repeated in connection with the device embodiments.

FIG. 5 shows a block diagram of a medical image analysis device according to an embodiment of the present disclosure. As shown in FIG. 5, the medical image analysis device may include a first receiving module 502 configured to receive a medical image acquired by a medical imaging device.

In some embodiments, the medical image analysis device may further include a navigation processing module 504 configured to perform a navigation processing on the medical image based on an analysis requirement to obtain a navigation trajectory, and the analysis requirement indicates a disease to be analyzed.

In some embodiments, the analysis requirement may include not only the disease to be analyzed, but also, for example, analysis requirements customized by the user according to different application scenarios.

In some embodiments, the medical image analysis device may further include a first extracting module 506 configured to extract an image block set along the navigation trajectory. In some embodiments, the navigation trajectory may include a template in which structural or functional regions are associated, and thus the image blocks in the extracted image block set may be also functionally or spatially associated.

In some embodiments, the medical image analysis device may further include a second extracting module 508 configured to extract image features by using a first learning network based on the image block set.

In some embodiments, the medical image analysis device may further include a first feeding module 510 configured to feed the extracted image features to a second learning network configured to determine an analysis result based on the image features and the navigation trajectory.

The medical image analysis device according to the embodiments of the present disclosure provides a model framework that can be uniformly applied to address different analysis requirements, thought the use of the navigation processing. For example, the model framework can analyze different diseases according to different requirements. The user can obtain respective navigation trajectories by inputting different analysis requirements (e.g., the types of disease), thus avoiding the complicated operation of changing different model settings according to the different requirements, and reducing the labor cost. Furthermore, by using the navigation trajectory, the disclosed analysis method can produce more useful information given a relatively small amount of input information. In other words, under the uniform framework, targeted and more representative information can be extracted from image blocks according to different analysis requirements. In addition, the method further determines the analysis result based on the image block set extracted along the navigation trajectory by using deep learning networks (e.g., the first learning network and the second learning network). As a result, medical images can be more accurately and efficiently analyzed according to the analysis requirements to provide more accurate and targeted diagnosis. Therefore, the complexity of medical image processing is reduced, and the efficiency and accuracy of medical image analysis are improved.

In some embodiments, the navigation trajectory is directional, and the image features are a sequence of image block features in the image block set. In some embodiments, the first learning network includes a convolutional neural network, and the second learning network includes one or a combination of a recurrent neural network and a recursive neural network.

In some embodiments, the analysis requirements further include a target region to be analyzed and a manual/automatic setting for navigation.

In some embodiments, the navigation trajectory includes a path or pattern of key points, or a template of structural or functional regions. The structural or functional regions in the template are associated with each other, corresponding to the analysis requirements.

In some embodiments, for the classification of fatty liver, the navigation trajectory is a path or pattern formed by more than one key point on the boundary of a liver and a kidney that are manually labelled/automatically detected.

In some embodiments, for vascular lesions detection, the navigation trajectory is the directional path of blood vessel segments formed by key points that are manually labelled/automatically detected, or a complete or partial blood vessel centerline that is automatically computed.

In some embodiments, for cerebral ischemia detection, the navigation trajectory is a template of structural or functional regions corresponding to left and right brains that are manually sketched/automatically detected.

In some embodiments, the image features are a sequence of image block features in the image block set. The second learning network is configured to learn a spatial/functional relationship among the image block features extracted by the first learning network based on the navigation trajectory, and determine the analysis result based on the learned spatial/functional relationship.

In some embodiments, the navigation processing uses a classification learning network established based on the training process of deep learning.

FIG. 6 shows a block diagram of a medical image analysis device according to an embodiment of the present disclosure. As shown in FIG. 6, the medical image analysis device may include a first receiving module 602 configured to receive a medical image acquired by a medical imaging device.

In some embodiments, the medical image analysis device may further include a navigation processing module 604 configured to perform the navigation processing on the medical image based on an analysis requirement to obtain a navigation trajectory, and the analysis requirement indicates a disease to be analyzed.

In some embodiments, the medical image analysis device may further include a first extracting module 606 configured to extract an image block set along the navigation trajectory.

In some embodiments, the medical image analysis device may further include a second extracting module 608 configured to extract image features by using a first learning network based on the image block set.

In some embodiments, the medical image analysis device may further include a first feeding module 610 configured to feed the extracted image features to a second learning network to determine an analysis result based on the image features and the navigation trajectory.

In some embodiments, the medical image analysis device may further include a second receiving module 612 configured to receive a medical record of a subject of the medical image.

In some embodiments, the medical image analysis device may further include a text screening module 614 configured to screen out texts relevant to the analysis requirements from the medical record.

In some embodiments, the medical image analysis device may further include a third extracting module 616 configured to extract text features based on the relevant texts.

In some embodiments, the medical image analysis device may further include a feature fusing module 618 configured to fuse the text features with the image features to obtain fused features.

In some embodiments, the medical image analysis device may further include a second feeding module 620 configured to feed the fused features to the second learning network configured to determine the analysis result based on the fused features.

In the medical image analysis device according to the embodiment of the present disclosure, the navigation trajectory is obtained by performing the navigation processing on the received medical image based on the analysis requirements, and the image features are extracted based on the image block set extracted along the navigation trajectory by using the first learning network. The text features extracted from the relevant texts screened out from the medical record are fused with the extracted image features to obtain the fused features, and the analysis result is determined based on the fused features by using the second learning network. Applying the second learning network to the fused features can reduce the interference of redundant information, so that medical images related to the analysis requirement can be analyzed more accurately and pertinently. Therefore, the disclosed method utilizes information more effectively, reduces complexity of the medical image processing, improves the efficiency and accuracy of the medical image analysis, and reduces the labor cost.

In some embodiments, the text features are extracted using a natural language processing model based on the relevant texts.

In some embodiments, the feature fusing module 618 is further configured to merge the text features with the image features, feed the merged features into a multilayer perceptron, and optimize the merged features through back propagation to obtain the fused features.

In some embodiments, the navigation processing uses a classification learning network established based on the training process of deep learning.

Figure 7:
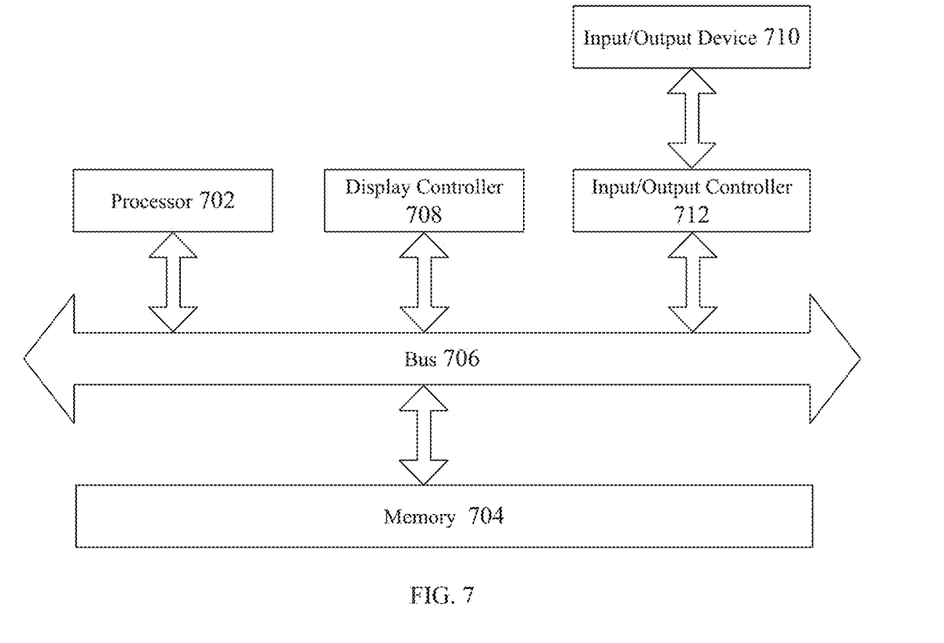
FIG. 7 shows a structural block diagram of a medical image analysis device according to an embodiment of the present disclosure.

FIG. 7 shows a structural block diagram of a medical image analysis device according to an embodiment of the present disclosure. As shown in FIG. 7, the medical image analysis may be a computer apparatus, such as a data processing device, including a computer hardware structure. The computer apparatus includes at least a processor 702 and a memory 704. The processor 702 and the memory 704 are connected through a bus 706. The memory 704 is adapted to store instructions or programs executable by the processor 702. The processor 702 may be an independent microprocessor or a set of one or more microprocessors. Thus, the processor 702 executes the method flow of the embodiments of the present disclosure as described above by executing commands stored in the memory 704, so as to realize the processing of data and the control of other devices. The bus 706 connects the above plurality of components together and connects the components to a display controller 708, a display device and an input/output (I/O) device 710. The input/output (I/O) device 710 may be a mouse, a keyboard, a modem, a network interface, a touch input device, a somatosensory input device, a printer, and other devices known in the art. Typically, the input/output (I/O) device 710 is connected to the system through an input/output (I/O) controller 712.

The memory 704 may store software components, such as an operating system, a communication module, an interaction module and an application program. Each of the modules and applications described above corresponds to achieving one or more functions and a set of executable program instructions of the method described in the embodiments of the present disclosure.

In some embodiments, the computer apparatus may be located at a centralized location, or distributed over many places. For example, the computer apparatus may sit in the cloud.

The flowcharts and/or block diagrams of methods, systems, and computer program products according to the embodiments of the present disclosure described above describe various aspects of the present disclosure. It should be understood that each block of the flowchart and/or block diagram and the combination of blocks in the flowchart illustrations and/or block diagram may be implemented by computer program instructions. These computer program instructions may be provided to a processor of a general-purpose computer, a special-purpose computer, or other programmable data processing apparatus to generate a machine such that instructions (executed via the processor of the computer or other programmable data processing apparatus) create means for implementing functions/actions specified in the flowcharts and/or block diagram blocks or blocks.

Meanwhile, as will be realized by those skilled in the art, various aspects of the embodiments of the present disclosure may be implemented as systems, methods or computer-readable media having computer-readable program code implemented thereon.

Any combination of one or more computer-readable media may be utilized. The computer-readable medium may be a non-transitory computer-readable storage medium. The computer-readable storage medium may be, for example, but not limited to, an electronic, magnetic, optical, electromagnetic, infrared or semiconductor system, apparatus or device, or any appropriate combination of the foregoing. More specific examples (non-exhaustive enumeration) of computer-readable storage media will include the following items: portable computer floppy disk, hard disk, random access memory (RAM), read only memory (ROM), erasable programmable read only memory (EPROM or flash memory), optical fiber, portable optical disk read only memory (CD-ROM), optical storage device, magnetic storage device, or any appropriate combination of the foregoing. In the context of the embodiments of the present disclosure, the computer-readable storage medium may be any non-transitory and tangible medium capable of containing or storing programs used by or in conjunction with an instruction execution system, apparatus or device.

The program code stored on the computer-readable medium may be transmitted using any suitable medium including, but not limited to, wireless, wired, optical fiber cable, RF, etc., or any suitable combination of the foregoing.

The computer program code for performing operations on various aspects of the present disclosure may be written in any combination of one or more programming languages, the programming languages including: object-oriented programming languages such as Java, Smalltalk, C++, PHP, Python, etc., and conventional process programming languages such as "C" programming language or similar programming languages. The program code may be completely and partially executed on the user computer as an independent software package; partially on the user computer and partially on the remote computer; or completely on the remote computer or server. In the latter case, the remote computer may be connected to the user computer through any type of network including a Local Area Network (LAN) or a Wide Area Network (WAN), or may be connected to an external computer (for example, through using the Internet of an Internet service provider).

These computer program instructions may also be stored in the computer-readable medium that can instruct computers, other programmable data processing apparatuses or other devices to operate in a specific manner, to perform the functions/methods described in the flowcharts and/or block diagrams above.

The computer program instructions may also be loaded into the computer, other programmable data processing apparatuses or other devices to perform a series of operable steps on the computer, other programmable apparatuses or other devices to produce a computer-implemented process, to perform the functions/methods described in the flowcharts and/or block diagram blocks.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. It is intended, therefore, that the descriptions are considered as examples only, with a true scope being indicated by the following claims and their equivalents.

The above description is intended to be illustrative, and not restrictive. For example, the above-described examples (or one or more aspects thereof) may be used in combination with each other. Other embodiments can be derived, such as by one of ordinary skill in the art upon reviewing the above description. Also, in the above Detailed Description, various features may be grouped together to streamline the disclosure. This should not be interpreted that any unclaimed disclosed feature should be imported into any claim. Rather, inventive subject matter may lie in less than all features of a disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with their equivalents.

What is claimed is:

1. A medical image analysis method, comprising:
   receiving a medical image acquired by a medical imaging device;
   determining a navigation trajectory by performing a navigation processing on the medical image based on an analysis requirement, the analysis requirement indicating a disease to be analyzed;
   extracting an image block set along the navigation trajectory;
   extracting image features using a first learning network based on the image block set extracted along the navigation trajectory;
   receiving a medical record of a subject of the medical image;
   screening out texts relevant to the analysis requirement from the medical record;
   extracting text features based on the relevant texts;
   fusing the text features and the image features to obtain fused features; and
   determining an analysis result using a second learning network based on the fused features and the navigation trajectory.

2. The medical image analysis method according to claim 1, wherein the navigation trajectory is directional, the image features include a sequence of image block features in the image block set, the first learning network comprises a convolutional neural network, and the second learning network comprises one or a combination of a recurrent neural network and a recursive neural network.

3. The medical image analysis method according to claim 1, wherein the analysis requirement further comprises at least one of a target region to be analyzed, a manual setting, or an automatic setting for navigation.

4. The medical image analysis method according to claim 1, wherein the navigation trajectory includes a path or pattern of key points, or a template of structural or functional regions that are associated with each other for the analysis requirement.

5. The medical image analysis method according to claim 1, wherein for a classification of fatty liver, the navigation trajectory is a path or pattern formed by more than one key points of a liver and a kidney that are manually labelled or automatically detected.

6. The medical image analysis method according to claim 1, wherein for a vascular lesion detection, the navigation trajectory is a directional path of blood vessel segments formed by key points that are manually labelled or automatically detected, or a complete or partial blood vessel centerline that is automatically computed.

7. The medical image analysis method according to claim 1, wherein for a cerebral ischemia detection, the navigation trajectory is a template of structural or functional regions corresponding to left and right brains that are manually sketched or automatically detected.

8. The medical image analysis method according to claim 1, wherein the image features include a sequence of image block features in the image block set,
   wherein the second learning network is configured to:
   learn at least one of a spatial relationship or a functional relationship based on the image features extracted by the first learning network and the navigation trajectory, and
   determine the analysis result based on the at least one of the spatial relationship or the functional relationship.

9. The medical image analysis method according to claim 1, wherein the text features are extracted based on the relevant texts using a natural language processing model.

10. The medical image analysis method according to claim 1, wherein fusing the text features and the image features to obtain the fused features further comprises:
    merging the text features and the image features to generate merged features, feeding the merged features into a multilayer perceptron, and optimizing the merged features through back propagation to obtain the fused features.

11. The medical image analysis method according to claim 1, wherein the navigation processing uses a classification learning network established based on a deep learning training process.

12. A medical image analysis device, comprising:
    an input/output device configured to receive a medical image acquired by a medical imaging device and a medical record of a subject of the medical image; and
    a processor configured to:
      determine a navigation trajectory by performing a navigation processing on the medical image based on an analysis requirement, wherein the analysis requirement indicates a disease to be analyzed;
      extract an image block set along the navigation trajectory;
      extract image features using a first learning network based on the image block set extracted along the navigation trajectory;
      screen out texts relevant to the analysis requirement from the medical record;
      extract text features based on the relevant texts;
      fuse the text features and the image features to obtain fused features; and
      determine an analysis result using a second learning network based on the fused features and the navigation trajectory.

13. The medical image analysis device according to claim 12, wherein the navigation trajectory is directional, the image features include a sequence of image block features in the image block set, the first learning network comprises a convolutional neural network, and the second learning network comprises one or a combination of a recurrent neural network and a recursive neural network.

14. The medical image analysis device according to claim 12, wherein the analysis requirement further comprises at least one of a target region to be analyzed, a manual setting, or an automatic setting for navigation.

15. The medical image analysis device according to claim 12, wherein the navigation trajectory includes a path or pattern of key points, or a template of structural or functional regions that are associated with each other for the analysis requirement.

16. The medical image analysis device according to claim 12, wherein the image features are a sequence of image block features in the image block set,
    wherein the second learning network is configured to learn at least one of a spatial relationship or a functional relationship based on the image features extracted by the first learning network and the navigation trajectory, and determine the analysis result based on the at least one of the spatial relationship or the functional relationship.

17. The medical image analysis device according to claim 12, wherein the navigation processing uses a classification learning network established based on a deep learning training process.

18. A non-transitory computer-readable storage medium on which computer program instructions are stored, wherein when executed by a processor the computer program instructions cause the processor to perform a medical image analysis method, the medical image analysis method comprising:
    receiving a medical image acquired by a medical imaging device;
    determining a navigation trajectory by performing a navigation processing on the medical image based on an analysis requirement, the analysis requirement indicating a disease to be analyzed;
    extracting an image block set along the navigation trajectory;
    extracting image features using a first learning network based on the image block set extracted along the navigation trajectory;
    receiving a medical record of a subject of the medical image;
    screening out texts relevant to the analysis requirement from the medical record;
    extracting text features based on the relevant texts;
    fusing the text features and the image features to obtain fused features; and
    determining an analysis result using a second learning network based on the fused features and the navigation trajectory.

* * * * *